United States Patent [19]

Makino et al.

[11] Patent Number: 5,114,853
[45] Date of Patent: May 19, 1992

[54] RECOMBINANT DNA, TRANSFORMANT CONTAINING SAID DNA, AND PROCESS FOR PREPARING HEAT-STABLE GLUCOSE DEHYDROGENASE BY USE OF SAID TRANSFORMANT

[75] Inventors: Yasutaka Makino, Suita; Seiji Negoro, Osaka; Itaru Urabe, Akashi; Hirosuke Okada, Osaka, all of Japan

[73] Assignee: Amano Pharmaceutical Co., Ltd., Aichi, Japan

[21] Appl. No.: 410,844

[22] Filed: Sep. 22, 1989

[30] Foreign Application Priority Data

Sep. 22, 1988 [JP] Japan .................. 62-237699

[51] Int. Cl.$^5$ .................. C12N 9/04; C12N 15/53; C12N 15/70; C12N 1/21
[52] U.S. Cl. .................. 435/190; 536/27; 435/320.1; 435/252.33; 935/10; 935/73
[58] Field of Search .................. 435/69.1, 172.1, 172.3, 435/190, 14; 935/14, 82

[56] References Cited

U.S. PATENT DOCUMENTS

| | | | |
|---|---|---|---|
| 3,964,974 | 6/1976 | Banauch et al. | 435/14 X |
| 4,120,755 | 10/1978 | Pierre et al. | 435/14 |
| 4,980,288 | 12/1990 | Bryan et al. | 435/172.3 X |

OTHER PUBLICATIONS

Nagao, T. et al., 1989, *FEBS Lett.* vol. 253, pp. 113–116.
Heilmann, H. J. et al., 1988, *Eur. J. Biochem.*, vol. 174, pp. 485–490.

*Primary Examiner*—Richard A. Schwartz
*Assistant Examiner*—Mary E. Mosher
*Attorney, Agent, or Firm*—Wegner, Cantor, Mueller & Player

[57] ABSTRACT

A recombinant DNA replicable and expressible in *Escherichia coli* is disclosed which encodes glucose dehydrogenase originating from *Bacillus megaterium*. A DNA sequence encoding the glucose dehydrogenase is incorporated into an *E. coli* vector and then used to transform an *E. coli* host. Also disclosed are transformants and recombinant DNA incorporating thermostable glucose dehydrogenase, wherein at least one amino acid in glucose dehydrogenase at positions 96, 252, and 253 is replaced by a thermostability-conferring amino acid.

9 Claims, 2 Drawing Sheets

FIG. 2

Met-Tyr-Lys-Asp-Leu-Glu-Gly-Lys-Val-Val-Val-Ile-Thr-Gly-Ser-Ser-Thr-Gly-Leu-Gly-
Lys-Ser-Met-Ala-Ile-Arg-Phe-Ala-Thr-Glu-Lys-Ala-Lys-Val-Val-Asn-Tyr-Arg-Ser-
Lys-Glu-Asp-Glu-Ala-Asn-Ser-Val-Leu-Glu-Glu-Ile-Lys-Lys-Val-Gly-Gly-Glu-Ala-Ile-
Ala-Val-Lys-Gly-Asp-Val-Thr-Val-Glu-Ser-Asp-Val-Ile-Asn-Leu-Val-Gln-Ser-Ala-Ile-
Lys-Glu-Phe-Gly-Lys-Leu-Asp-Val-Met-Ile-Asn-Asn-Ala-Gly-Leu-Glu-Asn-Pro-Val-Ser-
Ser-His-Glu-Met-Ser-Leu-Ser-Asp-Trp-Asn-Lys-Val-Ile-Asp-Thr-Asn-Leu-Thr-Gly-Ala-
Phe-Leu-Gly-Ser-Arg-Glu-Ala-Ile-Lys-Tyr-Phe-Val-Glu-Asn-Asp-Ile-Lys-Gly-Thr-Val-
Ile-Asn-Met-Ser-Ser-Val-His-Glu-Lys-Ile-Pro-Trp-Pro-Leu-Phe-Val-His-Tyr-Ala-Ala-
Ser-Lys-Gly-Gly-Met-Lys-Leu-Met-Thr-Glu-Thr-Leu-Ala-Leu-Glu-Tyr-Ala-Pro-Lys-Gly-
Ile-Arg-Val-Asn-Asn-Ile-Gly-Pro-Gly-Ala-Ile-Asn-Thr-Pro-Ile-Asn-Ala-Glu-Lys-Phe-
Ala-Asp-Pro-Gln-Glu-Arg-Ala-Asp-Val-Glu-Ser-Met-Ile-Pro-Met-Gly-Tyr-Ile-Gly-Glu-
Pro-Glu-Glu-Ile-Ala-Ala-Val-Ala-Ala-Trp-Leu-Ala-Ser-Ser-Glu-Ala-Ser-Tyr-Val-Thr-
Gly-Ile-Thr-Leu-Phe-Ala-Asp-Gly-Gly-Met-Thr-Gln-Tyr-Pro-Ser-Phe-Gln-Ala-Gly-Arg-Gly

RECOMBINANT DNA, TRANSFORMANT CONTAINING SAID DNA, AND PROCESS FOR PREPARING HEAT-STABLE GLUCOSE DEHYDROGENASE BY USE OF SAID TRANSFORMANT

BACKGROUND OF THE INVENTION

1. Field of the Invention

The present invention relates to an improved recombinant DNA capable being replicated in *Escherichia coli* in which an improved DNA obtained by substituting with a different amino acid an amino acid located at a specific position in an amino acid sequence of the DNA that codes for glucose dehydrogenase (hereinafter "GDH") originating from *Bacillus megaterium* has been integrated into an *Escherichia coli* DNA incorporating vector. It also relates to a transformant containing the same, and a process for preparing a heat-stable GDH by use of the same.

2. Related Background Art

GDH [EC 1.1.1.47] is an important enzyme used as an enzyme for glucose assay system in the field of clinical tests and food industries.

Hitherto known as microorganisms capable of producing GDH are bacteria of the genus Bacillus such as *Bacillus megaterium* and *Bacillus cereus* (Japanese Patent Laid-Open No. Sho 53-137199).

However, in order to use GDH as the glucose-quantitating enzyme, a GDH having better stability has been sought to be prepared at a lower cost.

Recently, European Journal of Biochemistry, Vol. 174, pp. 485–490 (1988) has disclosed a method of producing GDH by using a transformant in which GDH gene originating from *Bacillus megaterium* has been integrated into *Escherichia coli*.

It teaches that the GDH gene originating from *Bascilus megaterium* exists in plurality. The transformant is obtained by using them to produce GDH, but the vector used therefor is not suited to the mass production of GDH, and also no improvement has been made at all to more stabilize the GDH.

SUMMARY OF THE INVENTION

It is an object of the present invention to provide heat-stable GDH at a low cost and in a large quantity by culturing the transformant containing the improved recombinants DNA replicable in *Escherichia coli* in which an improved DNA obtained by substituting with a different amino acid an amid acid located at a specific position shown in an amino acid sequence of the DNA that codes for GDH originating from *Bacillus megaterium* has been integrated into an *Escherichia coli* DNA incorporating vector.

Aiming first at more inexpensively preparing GDH, the present inventors succeeded in highly producing GDH by integrating into a high expression-vector, PKK 233-3, a GDH gene originating from *Bacillus megaterium*, and culturing said transformant in a nutrient broth.

Thereafter, as a result of further studies, a transformant in which an improved DNA obtained by substituting with a different amino acid an amino acid sequence of the DNA that codes for GDH originating from *Bacillus megaterium* has been integrated into an *Escherichia coli* was cultured in a nutrient broth. As a result, the present inventors succeeded in producing GDH having a better heat-stability than the conventional GDH, in a large quantity in the broth. The present invention has been thus accomplished.

According to the present invention, there is provided an improved recombinant DNA replicable in *Escherichia coli* in which an improved DNA obtained by substituting with a different amino acid, an amino acid located at a specific position in the following amino acid sequence of the DNA that codes for glucose dehydrogenase originating from *Bacillus megaterium* has been integrated into an *Escherichia coli* incorporating vector.

Met—Tyr—Lys—Asp—Leu—Glu—Gly—Lys—Val—Val— 10
Val—Ile—Thr—Gly—Ser—Ser—Thr—Gly—Leu—Gly— 20
Lys—A—Met—Ala—Ile—Arg—Phe—Ala—Thr—Glu— 30
Lys—Ala—Lys—Val—Val—Val—Asn—Tyr—Arg—Ser— 40
Lys—Glu—X—Glu—Ala—Asn—Ser—Val—Leu—Glu— 50
Glu—Ile—Lys—Lys—Val—Gly—Gly—Glu—Ala—Ile— 60
Ala—Val—Lys—Gly—Asp—Val—Thr—Val—Glu—Ser— 70
Asp—Val—Ile—Asn—Leu—Val—Gln—Ser—Y—Ile— 80
Lys—Glu—Phe—Gly—Lys—Leu—Asp—Val—Met—Ile— 90
Asn—Asn—Ala—Gly—B—Glu—Asn—Pro—Val—Ser— 100
Ser—His—Glu—Met—Ser—Leu—Ser—Asp—Trp—Asn— 110
Lys—Val—Ile—Asp—Thr—Asn—Leu—Thr—Gly—Ala— 120
Phe—Leu—Gly—Ser—Arg—Glu—Ala—Ile—Lys—Tyr— 130
Phe—Val—Glu—Asn—Asp—Ile—Lys—Gly—Thr—Val— 140
Ile—Asn—Met—Ser—Ser—Val—His—Glu—Lys—Ile— 150
Pro—Trp—Pro—Leu—Phe—Val—His—Tyr—Ala—Ala— 160
Ser—Lys—Gly—Gly—Met—Lys—Leu—Met—Thr—Glu— 170
Thr—Leu—Ala—Leu—Glu—Tyr—Ala—Pro—Lys—Gly— 180
Ile—Arg—Val—Asn—Asn—Ile—Gly—Pro—Gly—Ala— 190
Ile—Asn—Thr—Pro—Ile—Asn—Ala—Glu—Lys—Phe— 200
Ala—Asp—Pro—Gln—Glu—Arg—Ala—Asp—Val—Glu— 210
Ser—Met—Ile—Pro—Met—Gly—Tyr—Ile—Gly—Glu— 220
Pro—Glu—Glu—Ile—Ala—Ala—Val—Ala—Ala—Trp— 230
Leu—Ala—Ser—Ser—Glu—Ala—Ser—Tyr—Val—Thr— 240
Gly—Ile—Thr—Leu—Phe—Ala—Asp—Gly—Gly—Met— 250
Thr—Gln—Tyr—Pro—Ser—Phe—Gln—Ala—Gly—Arg— 260
Gly (wherein A represents Ser or Ala, X represents Asp or Glu, Y represents Ala or Ser, and B represents Leu or Met.)

BRIEF DESCRIPTION OF THE DRAWINGS

FIG. 2 shows a DNA amino acid sequence of GDH originating from *Bacillus meqaterium* IWG3.

DETAILED DESCRIPTION OF THE PREFERRED EMBODIMENTS

Figure 1:
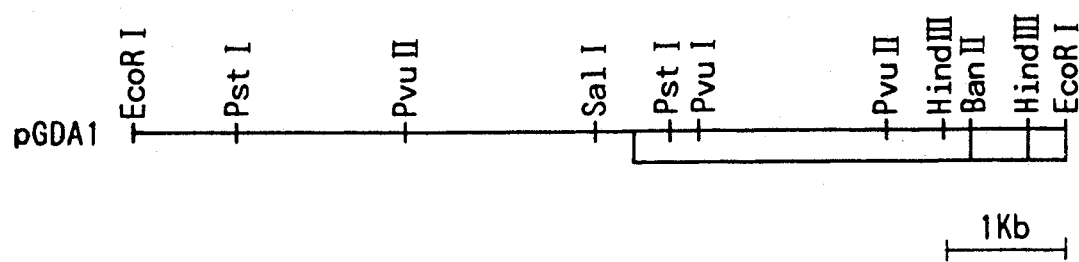
FIG. 1 shows a restriction endnuclease map of plasmid pGDA1.

In order to prepare the improved recombinant DNA of the GDH originating from *Bacillus megaterium*, it is necessary to first prepare a recombinant DNA that codes for the GDH.

As strains used therefor, any strains can be used so long as they are *Bacillus megateriums* capable of producing GDH, but it is preferred to use *Bacillus megaterium* IAM1030 and *Bacillus megaterium* IWG3 isolated from soil.

Of the above, the strain obtained from soil, *Bacillus megaterium* IWG3 is identified in the following way.

Results of identification

Tests for bacteriological properties were based on The Genus Bacillus (1973) by Ruth E. Gordon, and the classification was made in accordance with Bergey's Manual of Determinative Bacteriology, 8th Edition, and the above The Genus Bacillus.

A. Morphology (1) Bacillus with a cell size of 1.1 to 1.6μ×3.0 to 5.0μ. The insides of cells are granular when cells having grown in a glucose nutrient agar is dyed with fuchsine.
(2) No movement.
(3) Spores are formed with a size of 1.0 to 1.3μ×2.0 to 2.5μ, which are egg-like or column-like. Sporandia do not swell out. Spores are formed at the central part or the part near to ends.
(4) Gram stain: Positive

B. Physiological properties (1) Reduction of nitrate: Negative
(2) Denitrification: Negative
(3) VP test: Negative. The pH of the broth is 4.6 to 5.0 in the culture for 7 days.
(4) Formation of indole: Negative
(5) Hydrolysis of starch: Negative
(6) Utilization of citrate: Positive
(7) Utilization of inorganic nitrogen source: Both ammonium salt and nitrate are utilized.
(8) Formation of pigment: A brown water-soluble pigment is formed in a tyrosine medium.
(9) Urease: Weakly positive
(10) Catalase: Positive
(11) Behavior to oxygen: Aerobic
(12) Formation of acid and gas from saccharides: Acid is formed from arabinose, xylose, glucose, fractose, galactose, maltose, sucrose, lactose, trehalose, mannitol, inositol, glycerol and starch, but gas is not formed. Neither acid nor gas is formed from mannose and sorbitol.
(13) Growth in 7% NaCl medium: No detection
(14) Growth at 45° C.: Grow
(15) Growth at 65° C.: No detection
(16) Growth in Sabouraud dextrose medium: Grow
(17) Deamination of phenylalanine: Positive
(18) Liquefaction of gelatin: Positive
(19) Decomposition of casein: Positive
(20) Decomposition of tyrosine: Positive
(21) York reaction: Negative Reference of the above properties according to the classification method in Bergey's Manual of Determinative Bacteriology (8th Edition) finds that the present strain was classified into the genus Bacillus, since it is a gram-positive aerobic bacillus and forms spores. The species was identified as *Bacillus megaterium* on account of the properties that i) the nutrient cell size is 1.0 to 1.6μ×3.0 to 5.0μ and the insides of cells are granular in the glucose nutrient agar, ii) sporandia do not swell out, and spores are formed at the central part or the part near to ends., iii) acid is formed from glucose, and the VP test is negative, iv) no growth is seen under anaerobic conditions, v) growth is seen in Sabouraud dextrose medium, vi) acid is formed from arabinose, xylose and mannitol, and vii) york reaction is negative.

The present inventors named the present strain as *Bacillus megaterium* IWG3.

Preparation of transformant (1)

1) Purification of GDH

*Bacillus megaterium* IWG3 was inoculated in 2×TY broth. After the culture is completed, bacteria are collected and crushed, followed by centrifugal separation. The resulting supernatant is desalted, and then concentrated, followed by freeze-drying. The resulting GDH crude enzyme powder (105 μg) is dissolved in 15 ml of an imidazole buffer solution (20 mM, pH 6.5) containing 10% of glycerol, and adsorbed on DEAE-Sephadex A-50, followed by elution utilizing the sodium chloride concentration gradient (0.1 M–0.5 M) to collect active fractions, which are desalted and concentrated. Next, molecular fractionation is carried out by high performance liquid chromatography using TSK-gel DEAE 3 SW as a carrier, and adsorption and elution are further carried out by high performance liquid chromatography using TSK-gel G3000 SW as a carrier to obtain an electrophoretically uniform active fraction (about 5 mg as protein weight).

2) Determination of amino group-terminated amino acid sequence of GDH

The amino group-terminated amino acid sequence of the purified enzyme protein obtained according to the above procedure 1) was analyzed using a peptide sequencer Gas Phase 470A, manufactured by ABI (Applied Biosystem Inc.). Thus, the sequence of 29 amino acid residual groups from the N-terminal was determined. The amino group-terminated amino acid sequence thus obtained is shown below.

<u>Met—Tyr—Lys—Asp—Leu—Glu—Gly—Lys—Val—Val—Val—Ile—Thr—Gly</u>—Ser—Ser—Thr—Gly—Leu—Gly—Lys—Ser—Met—Ala—Ile—Arg—Phe—Ala—Thr

Remarks: The underlined portion shows the sequence used in the synthesis of probes.

3) Synthesis of DNA probe

A sequence at one site shown by the underline was selected from the above amino acid sequences. Among the possible DNA base sequences on genes, presumed from these amino acid sequences, a DNA base sequence was presumed making reference on the codon-utilizing frequency of *Bacillus subtilis*, and thus the base sequence of DNA probe of a sort of a 38 mer was determined as shown below.

TAC ATA TTT CTA GAC CTT CCT TTT CAA CAA CAA TAA TG

The synthesis of DNA was carried out by using Synthesizer Model 381A, manufactured by ABI.

4) Extraction of the whole DNA from *Bacillus megaterium*, and breakage thereof The whole DNA was extracted from *Bacillus megaterium* IWG3 and purified, according to the Saito and Miura's method [(Biochim. Biophys. Acta. Vol. 72, 619 (1963)]. 240 μg of the resulting DNA was taken, and reacted with 150 units each of restriction endnucleases EcoRI and BglII at 37° C. for 3 hours. The whole of the reaction mixture was subjected to 1% agarose gel electrophoresis, the part containing DNA corresponding to the size of 3 to 4 kb was cut out, and DNA fragments were eluted from the gel by electroextraction. Subsequently, the eluate was successively extracted by use of equimolar amounts of phenol and phenol-chloroform, and ethanol was added to the resulting aqueous layer to precipitate DNA, which was thereafter dissolved in 100 μl of a TE buffer solution.

5) Insertion of DNA fragment to vector

Used as the vector was pBR322, but linear vector DNA obtained as a result of complete decomposition of 20 μg of pBR322 with EcoRI-BamHI, dissolved in 200 μl of a TE buffer solution, was used for insertion of the DNA fragment. Joining to the DNA fragments obtained in the above step 4) was carried out by mixing the solution obtained in the step 4) and the linear vector DNA solution in a 10:1 proportion, and reacting T4 DNA ligase at 14° C. overnight.

6) Preparation of DNA library of *Bacillus megaterium*

The recombinant DNA obtained in the above step 5) was incorporated into the host *Escherichia coli* C600 by transformation, and colonies made to grow on an L-broth agar medium containing 50 μg/ml of ampicillin were collected, which were called a DNA library of *Bacillus megaterium* IWG3.

7) Selection and separation of GDH clone from DNA library

The DNA probes obtained in the above step 3) were each labelled by use of T4 polynucleotide kinase and γ-$^{32}$P-ATP, by the method according to the Ingria et al. [Nucleic Acids Research. Vol. 9, 1627-1642 (1982)]. Next, the *Escherichia coli* obtained in the above step 6) was grown to colonies on an L-broth agar medium containing 50 μg/ml of ampicillin, which were transferred by replica plating to an Amersham nylon membrane, followed by lysozyme bacteriolysis, DNA denaturation by use of alkali, neutralization by use of hydrochloric acid, and thereafter hybridization with the above probe. The hybridization was carried out by pre-hybridization using 6-fold concentrated SSC (0.15 M NaCl, 0.15 M sodium citrate, pH 7.0), a 5-fold concentrated Denhardt solution (0.02% Ficoll, 0.02% polyvinyl pyrrolidone, 0.02% bovine serum albumin), 0.5% SDS, 20 μg/ml (final concentration) of bovine thymus DNA and about $5 \times 10^5$ cpm/ml of the labelled DNA probe, which was carried out at 45° C. for 3 hours, and hybridization thereafter at 45° C. overnight. Thereafter, the nylon membrane was washed twice at 45° C. by use of a 5-fold concentrated SSC, subsequently twice at 45° C. by use of a 5-fold concentrated SSC (containing 0.1% SDS), and twice by use of a 4-fold concentrated SSC. The nylon membrane was thereafter dried, and subjected to autoradiography (conditions: −80° C., overnight). As a result, three colonies, which were hybridization-positive, were found. Now, liquid culture was carried out for the positive colonies, followed by the method according to Birnboim et al. [Nucleic Acids Research, Vol. 7, 1513-1523 (1979)] to prepare plasmid DNA. The resulting plasmid was cut by use of restriction endnucleases EcoRI and SalI, and subjected to agarose gel electrophoresis, followed by Southern hybridization [Journal of Molecular Biology, Vol. 98, 503-517 (1975)] with the labelled DNA. As a result, the DNA probe was found to be strongly hybridized with about 3.6 kb of DNA fragment produced by the breakage with EcoRI and SalI. The separated 3 strains were shown to have the same plasmid, and this plasmid was named pGDA1 as a candidate for the GDH clone.

8) Identification of GDH clone and determination of DNA base sequence

With regard to a 930 base pair of DNA fragment produced from the plasmid pGDA1 as a result of the breakage with EcoRI and Sau3AI, the DNA base sequence was determined by the method according to Sanger et al. [Proceedings of National Academy Science, U.S.A., Vol. 74, 5463-5467 (1977)]. As a result, there was found a base sequence that codes for an amino acid sequence completely coincident with the amino group-terminated amino acid sequence of the GDH obtained in the above step 2), and it was clarified that this fragment contains a part of the GDH genes. In respect of the plasmid pGDA1, a restriction endnuclease map as illustrated in FIG. 1 was made based on the results of the breakage with restriction endnucleases. The DNA base sequence located at the portion in the downstream direction from the base sequence already determined in which genes are read was determined. As a result, it was shown that there exists a base sequence that codes for a protein composed of 261 amino acids as shown in FIG. 2. From the foregoing results, it is presumed that structural genes of GDH are completely contained in the DNA fragment originating from *Bacillus megaterium* IWG3, present in the plasmid pGDA1.

9) Expression of GDH gene

In order to bring the cloned GDH genes into expression by use of *Escherichia coli*, expression of genes from the DNA fragment originating from *Bacillus megaterium* IWG3, present in the plasmid pGDA1, was attempted according to the following steps.

By use of EcoRI and PvuII, 10 μg of plasmid pGDA1 was cut, and subjected to 1% agarose electrophoresis to collect a fragment of about 1.5 kb. In 1 μg of the fragment obtained, dATP, dGTP, dCTP and dTTP, each in a final concentration of 1 mM, and 4 units of DNA polymerase Klenow fragment were added, and the reaction was carried out at 30° for 20 minutes in 20 μl of a reaction solution comprising a 10 mM tris-hydrochloric acid buffer solution (pH 7.5), 7 mM MgCl and 1 mM dithiothreitol. A DNA fragment having blunt end at each of both ends was thereby purified, and, in about 0.5 μg of the same, a PstI linker and 10 units of T4 DNA ligase were added, followed by reaction at 14° C. overnight in 20 μl of a reaction solution containing a 66 mM trishydrochloric acid buffer solution (pH 7.5), 5 mM MgCl$_2$, 5 mM dithiothreitol and 1 mM ATP. After the reaction, the DNA fragment was purified, and cut with BanII. Thereafter, in the resulting fragment, 1 U of Mung bean nuclease was added, followed by reaction at 30° C. for 30 minutes in 50 μl of a reaction solution (pH 4.5) containing 40 mM sodium acetate, 100 mM NaCl, 2 mM ZnCl₂ and 10% glycerol. As a result of this operation, the cohesive ends of BanII were made to blunt ends, and an EcoRI linker was further connected in the same manner as mentioned above. After the reaction, the DNA fragment was purified, and cut by use of EcoRI and PstI at its both ends, and collected as an EcoRI-PstI fragment.

An expression vector pKK223-3 used in the present example is reported by Brosius J. et al. [Proceedings of National Academy Science, U.S.A., Vol. 81, 6929–6933 (1984)], and had a tac promoter as a promoter.

This expression vector pKK223-3 was cut by use of restriction endnucleases EcoRI and PstI, and thereafter mixed with the collected EcoRI-PstI fragment to carry out the joining reaction by use of T4 DNA ligase. Using the reaction mixture, transformation of *Escherichia coli* JM105 was carried out, and colonies growing on an L-broth agar medium containing ampicillin (50 μg/ml) and isopropyl-β- D-thiogalactopyranoside (IPTG) were selected.

In order to confirm the expression of GDH for the colonies obtained, the colony assay using a dye coupling method was carried out. The colonies were replica-plated on a filter paper, and then a lysozyme solution (a 50 mM tris-hydrochloric acid buffer solution (pH 7.5), 10 mM EDTA, 1 mg/ml lysozyme), was added to the colonies on the filter paper. The resulting colonies were maintained at a temperature of 30° C. for 20 minutes, followed by addition of a 1% Triton solution, and were left to stand at room temperature for 5 minutes. A buffer solution for heat treatment [a 50 mM phosphate buffer solution (pH 6.5), 2 M NaCl, 50 mM EDTA] was further added to carry out heat treatment at 60° C. for 20 minutes.

Figure 3:
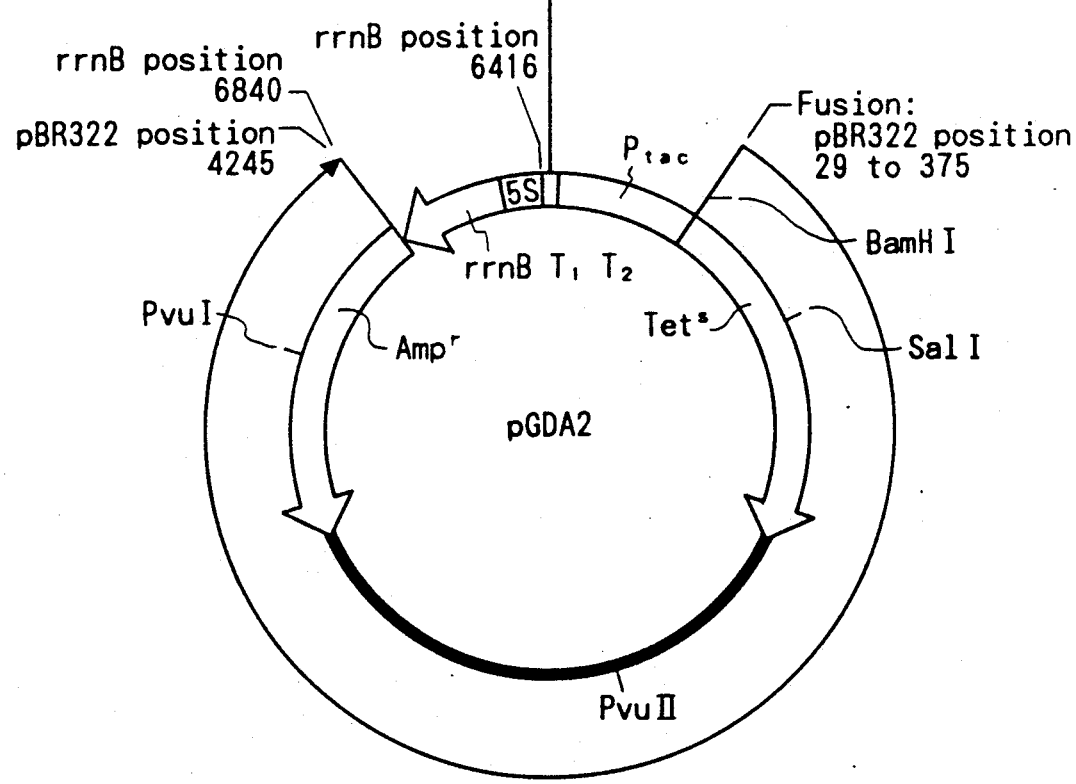
FIG. 3 shows a restriction endnuclease map of plasmid pGDA2.

Next, a substrate solution [20 mM tris-hydrochloric acid buffer solution (pH 8.0), 1 M NaCl, 100 mM glucose, 0.5 mM phenazine ethosulfate (PES), 0.5 mM 3-(4′,5′-dimethylthiazol-2-yl-2,5-diphenyltetrazolium bromide (MTT), 50 μM AND] was added, and the mixture was left to stand at 37° C. for 5 minutes in the dark. As a control, a solution corresponding to the above substrate solution except that the glucose was absent was used. The reaction was stopped by adding a 10% acetic acid solution. In selecting colonies, colonies having turned blue-violet were selected. As a result of colony assay, a number of positive colonies were obtained and plasmid DNA was extracted from one strain among them. The resulting extract was named pGDA2, and an expected structure (FIG. 3) was confirmed by breakage using restriction endnucleases.

The present plasmid was incorporated into *Escherichia coli* JM105 by transformation to obtain a GDH high-expression strain, *Escherichia coli* JM105/pGDA2.

The present strain has been deposited in Fermentation Research Institute, Agency of Industrial Science and Technology, under FERM-BP No. 2584.

Preparation of transformant (2)

Using *Bacillus megaterium* IAM1030 in place of *Bacillus megaterium* IWG3, the same procedures from 1) to 9) in Preparation of transformant (1) were repeated to extract highly GDH-expression plasmid DNA, which was named pGDA3. Subsequently, transformation of the present plasmid was carried out to obtain GDH high expression *Escherichia coli* JM105/pGDA3.

The amino acid sequence of the GDH obtained from *Bacillus megaterium* IAM1030, when compared with the DNA amino acid sequence shown in FIG. 2, of the GDH originating from *Bacillus megaterium* IWG3, was found to be no more than an amino acid sequence in which the serine at the 22-position from the latter's N-terminal was substituted with alanine, the aspartic acid at the 43-position with glutamic acid, the alanine at the 79-position with serine, and the leucine at the 95-position with methionine.

More specifically, the amino acid sequence of the DNA that codes for the GDH originating from *Bacillus megaterium* is summarized as follows:

```
                                          10
Met—Tyr—Lys—Asp—Leu—Glu—Gly—Lys—Val—Val—
                                          20
Val—Ile—Thr—Gly—Ser—Ser—Thr—Gly—Leu—Gly—
                                          30
Lys—A—Met—Ala—Ile—Arg—Phe—Ala—Thr—Glu—
                                          40
Lys—Ala—Lys—Val—Val—Val—Asn—Tyr—Arg—Ser—
                                          50
Lys—Glu—X—Glu—Ala—Asn—Ser—Val—Leu—Glu—
                                          60
Glu—Ile—Lys—Lys—Val—Gly—Gly—Glu—Ala—Ile—
                                          70
Ala—Val—Lys—Gly—Asp—Val—Thr—Val—Glu—Ser—
                                          80
Asp—Val—Ile—Asn—Leu—Val—Gln—Ser—Y—Ile—
                                          90
Lys—Glu—Phe—Gly—Lys—Leu—Asp—Val—Met—Ile—
                                          100
Asn—Asn—Ala—Gly—B—Glu—Asn—Pro—Val—Ser—
                                          110
Ser—His—Glu—Met—Ser—Leu—Ser—Asp—Trp—Asn—
                                          120
Lys—Val—Ile—Asp—Thr—Asn—Leu—Thr—Gly—Ala—
                                          130
Phe—Leu—Gly—Ser—Arg—Glu—Ala—Ile—Lys—Tyr—
                                          140
Phe—Val—Glu—Asn—Asp—Ile—Lys—Gly—Thr—Val—
                                          150
Ile—Asn—Met—Ser—Ser—Val—His—Glu—Lys—Ile—
                                          160
Pro—Trp—Pro—Leu—Phe—Val—His—Tyr—Ala—Ala—
                                          170
Ser—Lys—Gly—Gly—Met—Lys—Leu—Met—Thr—Glu—
                                          180
Thr—Leu—Ala—Leu—Glu—Tyr—Ala—Pro—Lys—Gly—
                                          190
Ile—Arg—Val—Asn—Asn—Ile—Gly—Pro—Gly—Ala—
                                          200
Ile—Asn—Thr—Pro—Ile—Asn—Ala—Glu—Lys—Phe—
                                          210
Ala—Asp—Pro—Gln—Glu—Arg—Ala—Asp—Val—Glu—
                                          220
Ser—Met—Ile—Pro—Met—Gly—Tyr—Ile—Gly—Glu—
                                          230
Pro—Glu—Glu—Ile—Ala—Ala—Val—Ala—Ala—Trp—
                                          240
Leu—Ala—Ser—Ser—Glu—Ala—Ser—Tyr—Val—Thr—
                                          250
Gly—Ile—Thr—Leu—Phe—Ala—Asp—Gly—Gly—Met—
                                          260
Thr—Gln—Tyr—Pro—Ser—Phe—Gln—Ala—Gly—Arg—
Gly
```

(wherein A represents Ser or Ala, X represents Asp or Glu, Y represents Ala or Ser, and B represents Leu or Met.)

Preparation of improved recombinant DNA (1)

1) Preparation of single-stranded DNA

The above plasmid pGDA2 or pGDA3 was cut by use of the restriction endnucleases EcoRI and PstI to obtain about 0.9 kb of GDH gene fragment, followed by cloning with M13 phage mp18 or mp19. From the resulting recombinant, a single-strand DNA was prepared by a conventional method.

2) Variation treatment of single-stranded DNA, by use of chemical reagent

In 50 µl of a 0.5 M acetate buffer solution (pH 4.3), 40 µg of the single-stranded DNA obtained in the above step was dissolved, and 50 µl of a 2 M sodium nitrite solution was added to the resulting solution to carry out treatment at 20° C. for 1 to 3 hours.

Similarly, 100 µl of a 12 M formic acid solution was added in place of the sodium nitrite solution to carry out treatment at 20° C. for 5 to 20 minutes. In addition thereto, 100 µl of a 60% hydrazine solution was added to similarly carry out treatment at 20° C. for 5 to 20 minutes. The reaction was stopped by addition of 100 µl of a 2.5 M acetate buffer solution (pH 7.0) containing 20 µg of tRNA to each of the above treatment solution. Subsequently, 200 µl of distilled water was added to each reaction mixture, followed by addition of 1 ml of ice-cooled ethanol to precipitate variation treated DNA, which was further washed three times with an ice-cooled 70% aqueous ethanol.

3) Preparation of variant double-stranded DNA fragment

To 10 µg of the variation-treated DNA obtained in the preceding step, 10 µl of a 10-fold concentrated buffer solution used for reverse transcriptase [a 70 mM tris-hydrochloric acid buffer solution (pH 7.5), 70 mM magnesium chloride, 0.5 M sodium chloride and 20 mM dithiothreitol], 2 µl of a solution containing 20 pmol of a primer and 74 µl of distilled water were added. The mixture was maintained at a temperature of 85° C. for 5 minutes and then at a temperature of 40° C. for 15 minutes, followed by addition of 13 µl of a 10 mM dNTP solution and 1 µl (20µ) of reverse transcriptase to carry out reaction at 37° C. After 1 hour, the reaction mixture was extracted with phenol, followed by precipitation with ethanol. The precipitate was dissolved, and thereafter decomposed by use of restriction endnucleases EcoRI and PstI, followed by agarose gel electrophoresis, and then variant double-stranded DNA fragment was collected from the gel according to a conventional method.

4) Selection of strain holding thermally stabilized GDH gene

The variant double-stranded DNA fragment obtained in the preceding step was integrated to the expression vector pKK223 at the sites cut with EcoRI and PstI to transform *Escherichia coli* JM103. Colonies having grown on a laboratory dish medium were examined for their enzymatic activities according to the replica printing method using a filter paper. The filter paper had been previously subjected to heat treatment at 60° C. for 20 minutes. The clone that showed a strong color formation on the filter paper was considered to have been thermally stabilized as a result of changes of the genes of GDH due to the variation, and thus the corresponding strains were picked up.

Next, the strains selected by the above method were each inoculated in to a 5 ml 2×TY medium to carry out shaking culture at 37° C. for 18 hours. After bacteria were collected and washed, the bacterial suspension was subjected to the ultrasonic treatment, followed by the centrifugal separation to obtain a supernatant. Heat treatment was carried out on this supernatant at 60° C. for 20 minutes, and residual activities were measured to select strains holding thermally stabilized variant enzyme genes.

5) Determination of base sequence of thermally stabilized variant enzyme genes, and identification of variation Plasmid DNA was prepared from the strains holding thermally stabilized variant enzyme genes, the base sequence of gene fragments was determined according to a conventional method to clarify variation sites, and thus changes on the amino acid sequence of enzyme proteins were confirmed.

More specifically, there were obtained an improved recombinant DNA, pGDA2F-18, in which the glutamic acid at the 96-position from the N-terminal of the amino acid sequence of GDH natural DNA originating from *Bacillus meqaterium* IWG3 has been changed to alanine; similarly, improved recombinant DNAs, pGDA2H-35, in which the glutamic acid at the 96-position from the N-terminal has been changed to glycine; pGDA2F-20, in which the glutamic acid at the 252-position from the N-terminal has been changed to leucine; pGDA2N-71, in which the tyrosine at the 253-position from the N-terminal has been changed to cystein; pGDA2N-1, in which the glutamic acid at the 96-position from the N-terminal and the valine at the 183-position from the N-terminal have been changed to lysine and isoleucine, respectively; pGDA2N-13, in which the glutamic acid, valine, glutamic acid and tyrosine at the 96-position, 112-position, 133-position and 217-position from the N-terminal have been changed to lysine, alanine, lysine and histidine, respectively; and also pGDA2N-28, in which the glutamic acid, aspartic acid, proline and glutamic acid at the 96-position, 108-position, 194-position and 210-position from the N-terminal have been changed to lysine, asparagine, glutamine and lysine, respectively. Subsequently, each transformant obtained by transformation of *Escherichia coli* JM103 with each plasmid was cultured at 37° C. for 18 hours in a 2×TY broth medium. After bacteria were collected, the bacterial suspension was subjected to the ultrasonic treatment, followed by the centrifugal separation. On the resulting supernatant, having been treated at 50° C. for 20 minutes and at 60° C. for 20 minutes, the residual GDH activities were measured.

As a control, comparison was made by use of an *Escherichia coli* JM103/pGDA2 strain. Results obtained are shown in Table 1.

TABLE 1

| Name of transformant | Variation site | GDH residual activities Treatment 50° C., 20 min % | 60° C. 20 min % |
|---|---|---|---|
| *Escherichia coli* | | | |
| JM103/pGDA2F-18 | Glu96 → Ala | 79 | 75 |
| JM103/pGDA2H-35 | Glu96 → Gly | 71 | 64 |
| JM103/pGDA2F-20 | Gln252 → Leu | 75 | 18 |
| JM103/pGDA2N-71 | Try253 → Cys | 61 | 3 |
| JM103/pGDA2N-1 | Glu96 → Lys Val183 → Ile | 77 | 59 |
| JM103/pGDA2N-13 | Glu96 → Lys Glu133 → Lys Val112 → Ala Tyr217 → His | 74 | 65 |
| JM103/pGDA2N-28 | Glu96 → Lys Pro194 → Gln | 76 | 68 |

TABLE 1-continued

| Name of transformant | Variation site | GDH residual activities Treatment | |
|---|---|---|---|
| | | 50° C., 20 min % | 60° C. 20 min % |
| JM103/pGDA2 | Asp108 → Asn Glu210 → Lys None | 3 | 0 |

As will be evident from Table 1, the heat stability of GDH is remarkably improved when a specific amino acid shown in the amino acid sequence that codes for GDH, i.e., the glutamic acid at the 96-position from the N-terminal, is substituted with any of alanine, glycine or lysine, or also when the glutamine at the 252-position from the N-terminal is substituted with leucin, and when the tyrosine at the 253-position from the N-terminal is substituted with cysteine.

Preparation of improved recombinant DNA (2)

The procedures from 1) to 5) in the paragraph of "Preparation of improved recombinant DNA (1)" were repeated except for the use of plasmid pGDA3 in place of plasmid pGDA2, to obtain an improved recombinant DNA, pGDA3F-20, in which the glutamic acid at the 96-position from the N-terminal of the amino acid sequence of the natural DNA originating from Bacillus megaterium IAM1030 has been changed to alanine; pGDA3F-20, in which the glutamine at the 252-position from the N-terminal has been changed to leucine; and pGDA3N-71, in which the tyrosine at the 253-position from the N-terminal has been changed to glycine; respectively.

Subsequently, each transformant obtained by transformation of Escherichia coli JM103 with each plasmid was cultured at 37° C. for 18 hours in a 2×TY broth medium. After bacteria were collected, the bacterial suspension was subjected to the ultrasonic treatment, followed by the centrifugal separation. On the resulting supernatant, having been treated at 50° C. for 20 minutes and at 60° C. for 20 minutes, the residual GDH activities were measured.

As a control, comparison was made by use of an Escherichia coli JM103/pGDA3 strain. Results obtained are shown in Table 2.

TABLE 2

| Name of transformant | Variation site | GDH residual activities Treatment | |
|---|---|---|---|
| | | 50° C., 20 min % | 60° C. 20 min % |
| Escherichia coli | | | |
| JM103/pGDA3F-18 | Glu96 → Ala | 76 | 68 |
| JM103/pGDA3F-20 | Gln252 → Leu | 69 | 14 |
| JM103/pGDA3N-71 | Try253 → Cys | 68 | 7 |
| JM103/pGDA3 | None | 2 | 0 |

Transformation to GCA, of base sequence GAA corresponding to the glutamic acid at the 96-position from the N-terminal of DNA of GDH originating from Bacillus megaterium IWG3

Using a site specific conversion method [M. Soller and M. Smith; Nucleic Acids Research, Vol. 10, 6487 (1982)], the base sequence GAA corresponding to the glutamic acid at the 96-position from the N-terminal of GDH genes was converted to GCA (alanine) to prepare variant genes. Heat stability of the enzyme produced in the same manner as described above was examined. As a result, a high heat stability was confirmed.

EXAMPLE 1

The transformant Escherichia coli JM105/pGDA2F18 was inoculated into 100 ml of a 2×TY broth containing 50 μg/ml of ampicillin to carry out shaking culture at 37° C. for 13 hours. Thereafter, IPTG (final concentration: 0.1 M) was added. After 2 hours, bacteria were collected by the centrifugal separation, washed with a 50 mM phosphate buffer solution (pH 6.5) containing 2 M of NaCl, and thereafter suspended in 10 ml of the like buffer solution. The resulting suspension was crushed by use of an ultrasonic crusher, followed by the centrifugal separation to obtain a supernatant (an enzyme solution). On the other hand, as a control, Bacillus megaterium IWG3 was inoculated into 100 ml of a 2×TY broth to carry out shaking culture at 37° C. for 24 hours. Next, in the same manner as the above, bacteria were collected, washed, and thereafter subjected to ultrasonic crushing, followed by the centrifugal separation. The resulting supernatant was used as an enzyme solution.

Enzymatic activities were measured by examining an increase in absorbance at 340 nm when the enzyme solution is added to a tris-hydrochloric acid buffer solution (pH 8.0) containing 0.1 M of D-glucose and 20 mM of AND to carry out the reaction at 30° C. in a photometer cell. The enzymatic activity capable of producing 1 μmole of NADH during the reaction for 1 minute was set as one unit. The specific activity was indicated as the unit per 1 mg of protein contained in the enzyme solution. As a result, the specific activity of Escherichia coli JM105/pGDA2F-18 was found to be 7.8 μ/mg. On the other hand, the specific activity of Bacillus megaterium IWG3 was found to be 0.07 μ/mg.

EXAMPLE 2

An enzyme solution of heat-stable GDH originating from an Escherichia coli JM105/pGDA2F-18 strain, and as a control an enzyme solution of GDH originating from a Bacillus megaterium IWG3 strain were compared to examine respectively the stability at 37° C. for 6 months.

As a result, the heat-stable GDH of transformant showed a residual activity of 90% or more, but the control showed a residual activity of 80% or less.

EXAMPLE 3

The transformant Escherichia coli JM105/pGDA3F-18 was inoculated into 100 ml of a 2×TY broth containing 50 μg/ml of ampicillin to carry out shaking culture at 37° C. for 13 hours. Thereafter, IPTG (final concentration: 0.1 M) was added. After 2 hours, bacteria were collected by the centrifugal separation, washed with a 50 mM phosphate buffer solution (pH 6.5) containing 2M of NaCl, and thereafter suspended in 10 ml of the like buffer solution. The resulting suspension was crushed by use of an ultrasonic crusher, followed by the centrifugal separation to obtain a supernatant.

The specific activity of the above supernatant was determined following the specific activity-measuring method of Example 1, to find that it was 6.6 μ/mg.

As having been described in the above, the present invention has made it possible to provide heatstable GDH at a low cost and in a large quantity by culturing the transformant containing the improved recombinant DNA replicable in *Escherichia coli* in which an improved DNA obtained by substituting with a different amino acid an amino acid located at a specific position shown in an amino acid sequence of the DNA that codes for GDH originating from *Bacillus megaterium* has been integrated into an *Escherichia coli* DNA incorporating vector.

We claim:

1. An isolated DNA fragment encoding a thermostable glucose dehydrogenase, said thermostable glucose dehydrogenase having the following amino acid sequence:

```
                                          10
Met—Tyr—Lys—Asp—Leu—Glu—Gly—Lys—Val—Val—
                                          20
Val—Ile—Thr—Gly—Ser—Ser—Thr—Gly—Leu—Gly—
                                          30
Lys—A—Met—Ala—Ile—Arg—Phe—Ala—Thr—Glu—
                                          40
Lys—Ala—Lys—Val—Val—Val—Asn—Tyr—Arg—Ser—
                                          50
Lys—Glu—X—Glu—Ala—Asn—Ser—Val—Leu—Glu—
                                          60
Glu—Ile—Lys—Lys—Val—Gly—Gly—Glu—Ala—Ile—
                                          70
Ala—Val—Lys—Gly—Asp—Val—Thr—Val—Glu—Ser—
                                          80
Asp—Val—Ile—Asn—Leu—Val—Gln—Ser—Y—Ile—
                                          90
Lys—Glu—Phe—Gly—Lys—Leu—Asp—Val—Met—Ile—
                                          100
Asn—Asn—Ala—Gly—B—Glu—Asn—Pro—Val—Ser—
                                          110
Ser—His—Glu—Met—Ser—Leu—Ser—Asp—Trp—Asn—
                                          120
Lys—Val—Ile—Asp—Thr—Asn—Leu—Thr—Gly—Ala—
                                          130
Phe—Leu—Gly—Ser—Arg—Glu—Ala—Ile—Lys—Tyr—
                                          140
Phe—Val—Glu—Asn—Asp—Ile—Lys—Gly—Thr—Val—
                                          150
Ile—Asn—Met—Ser—Ser—Val—His—Glu—Lys—Ile—
                                          160
Pro—Trp—Pro—Leu—Phe—Val—His—Tyr—Ala—Ala—
                                          170
Ser—Lys—Gly—Gly—Met—Lys—Leu—Met—Thr—Glu—
                                          180
Thr—Leu—Ala—Leu—Glu—Tyr—Ala—Pro—Lys—Gly—
                                          190
Ile—Arg—Val—Asn—Asn—Ile—Gly—Pro—Gly—Ala—
                                          200
Ile—Asn—Thr—Pro—Ile—Asn—Ala—Glu—Lys—Phe—
                                          210
Ala—Asp—Pro—Gln—Glu—Arg—Ala—Asp—Val—Glu—
                                          220
Ser—Met—Ile—Pro—Met—Gly—Tyr—Ile—Gly—Glu—
                                          230
Pro—Glu—Glu—Ile—Ala—Ala—Val—Ala—Ala—Trp—
                                          240
Leu—Ala—Ser—Ser—Glu—Ala—Ser—Tyr—Val—Thr—
                                          250
Gly—Ile—Thr—Leu—Phe—Ala—Asp—Gly—Gly—Met—
                                          260
Thr—Gln—Tyr—Pro—Ser—Phe—Gln—Ala—Gly—Arg—
Gly
``` wherein A represents Ser or Ala, X represents Asp or Glu, Y represents Ala or Ser, and B represents Leu or Met; and wherein Z1, Z2, and Z3, each represent a thermostability-conferring amino acid, provided that Z1, Z2, and Z3 taken together cannot be Glu, Gln, and Tyr, respectively.

2. A recombinant DNA replicable and expressible in *Escherichia coli* comprising an *E. coli* vector and the isolated DNA fragment of claim 1.

3. A recombinant DNA replicable and expressible in *Escherichia coli* comprising an *E. coli* vector and the isolated DNA fragment of claim 1, wherein Z1 is Lys, Gly or Ala.

4. *Escherichia coli* transformed with the recombinant DNA of claim 3.

5. A process for preparing heat-stable glucose dehydrogenase, comprising
culturing in a nutrient broth the transformant of claim 4,
producing heat-stable glucose dehydrogenase in a culture product, and
recovering the heat-stable glucose dehydrogenase from said culture product.

6. A recombinant DNA replicable and expressible in *Escherichia coli* comprising an *E. coli* vector and the isolated DNA fragment of claim 1, wherein Z2 is Leu.

7. *Escherichia coli* transformed with the recombinant DNA of claim 6.

8. A recombinant DNA replicable and expressible in *Escherichia coli* comprising an *E. coli* vector and the isolated DNA fragment of claim 1, wherein Z3 is Cys.

9. *Escherichia coli* transformed with the recombinant DNA of claim 8.

* * * * *